United States Patent [19]
Mora

[11] Patent Number: 4,596,824
[45] Date of Patent: Jun. 24, 1986

[54] P-AMINOPHENOL WITH MUCOSECRETOLYTIC-FLUIDIZING AND ANTIPYRETIC ACTIVITY, A PROCESS FOR ITS PREPARATION AND PHARMACEUTICAL COMPOSITIONS THEREOF

[75] Inventor: Camillo C. Mora, Piacenza, Italy

[73] Assignee: Camillo Corvi S.p.A., Italy

[21] Appl. No.: 711,953

[22] Filed: Mar. 14, 1985

[30] Foreign Application Priority Data

Apr. 2, 1984 [IT] Italy ................................. 20355 A/84

[51] Int. Cl.$^4$ ..................... A61K 31/24; C07C 69/732
[52] U.S. Cl. ........................................ 514/538; 560/43
[58] Field of Search .......................... 560/43; 514/538; 568/823

[56] References Cited

FOREIGN PATENT DOCUMENTS

| 764323 | 8/1971 | Belgium | 568/823 |
| 649603 | 10/1962 | Canada | 568/823 |
| 1096348 | 1/1961 | Fed. Rep. of Germany | 568/823 |

Primary Examiner—Natalie Trousof
Assistant Examiner—Bruce D. Gray
Attorney, Agent, or Firm—Ostrolenk, Faber, Gerb & Soffen

[57] ABSTRACT

There is described a novel acylamide derivative of p-aminophenol as obtained by condensation of 5-(3-carboxy-1-oxo-propoxy)-$\alpha,\alpha$-4, trimethyl-3-cyclohexene-1-methanol acid with p-aminophenol.

There are also described pharmaceutical compositions containing the novel p-aminophenol derivative with mucosecretolytic-fluidizing and antipyretic activity.

3 Claims, No Drawings

P-AMINOPHENOL WITH MUCOSECRETOLYTIC-FLUIDIZING AND ANTIPYRETIC ACTIVITY, A PROCESS FOR ITS PREPARATION AND PHARMACEUTICAL COMPOSITIONS THEREOF

DESCRIPTION

The subject of this invention is an acylamide derivative of p-aminophenol and precisely 5- [3-N-[(4-hydroxyphenyl) carboxamido]-1-oxo-propxy]-α,α-4-trimethyl-3-cyclohexene-1-methanol (Code:CO/1499) having the formula:

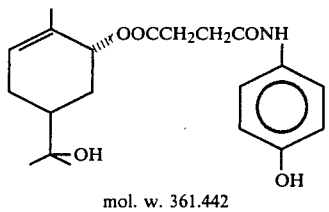

mol. w. 361.442 d,1-trans sobrerol, the terpene moiety of which occurs in the compound of formula (I) is well known because of its use in therapy in the respiratory diseases since it operates as a mucoregulator and expectorant agent.

It has now been found, unexpectedly, that the amide compound (I) of p-aminophenol, corresponding to the molecule of formula (I), being the subject of the present invention, beside a potency increase of the mucosecretolytic-fluidizing activity which may be ascribed to the d,1-trans-sobrerol moiety, performs a good activity useful in the fever complications which may arise together with the respiratory tract diseases.

The novel molecule is a bifunctional product, perfectly balanced for the chemical-pharmaceutical dosage. As regards the antipyretic activity, the novel molecule operates as the equivalent of a dose of either paracetamol or any drug of the same therapeutical class.

An object of this invention is, further, to provide a process for preparing the novel bifunctional molecule, which consists of condensing the 5-(3-carboxy-1-oxopropxy) α,α, 4-trimethyl-3-cyclohexene-1-methanol acid of formula (II) with p-aminophenol of formula (III)

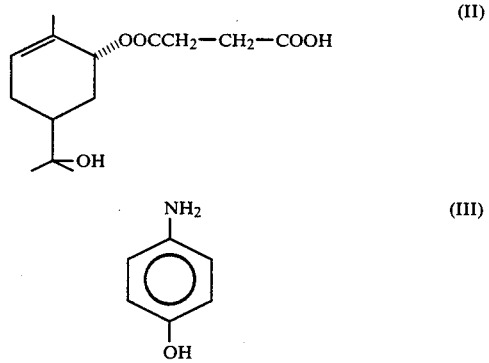

The condensation occurs in any aprotic solvent such as tetrahydrofuran, dioxane, ether, anhydrous methylene chloride free from ethanol, in the presence of a reactive product as a dehydrating agent, such as, in particular, N,N'-carbonyl-diimidazole, having the formula:

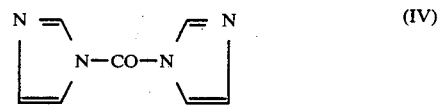

The process is carried out during about 16 hours under stirring within a temperature range from 20° to 25° C.

After the usual operations of neutralization, extraction, dehydration and concentration, the product of formula (1), as precipitated at a very good yield and purity degree, is obtained.

The process is illustrated in Example 1, as a non-limiting embodiment therefor:

EXAMPLE 1

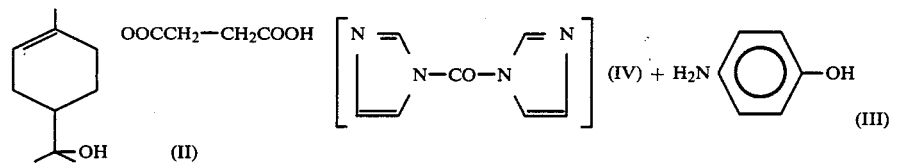

| $C_{14}H_{22}O_5$ | $C_7H_6N_4O$ | $C_6H_7NO$ |
| mol. wt. 270.32 | mol. wt. 162.15 | mol. wt. 109.12 |

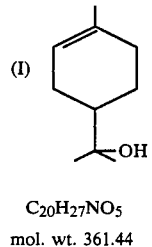

$C_{20}H_{27}NO_5$
mol. wt. 361.44

To a solution of 27 g (0.1 mole) of 5-(3-carboxy-1-oxopropxy) α,α,-4-trimethyl-3-cyclohexene-1-methanol acid (II) dissolved into 250 ml of tetrahydrofuran, 16.2 g (0.1 mole) of N,N'-carbonyl-diimidazole are added. It is left under stirring at 20°–25° C. over 4 hours and then 10.9 g (0.1 mole) of p-aminophenol are added.

The reaction mixture is left under stirring overnight and then it is pored into 600 ml of aqueous 5% sulphuric acid. After stirring a further ¼ hour, it is extracted with ethyl acetate (3×250 ml). The combined organic phases are washed with an aqueous 5% sodium bicarbonate solution and then with water.

The mixture is dried with anhydrous magnesium sulphate and is concentrated to a volume of about 200 ml. It is cooled with ice-water and the white crystalline produce (m.p. 164°–166° C.) as precipitated is filtered out.

Output 32 g
Yield % = 89% of theoretical

Analytical characterization of the compound of formula (I) of this invention

1. Elemental analysis for $C_{20}H_{27}NO_5$ mol.w. 361.442: Calculated % C=66.46, H=7.53, N=3.88, O=22. Found % C=66.36, H=7.58, N=3.78. (Average from 3 determinations)

2. I.R. Spectrum (Nujol dispersion; $cm^{-1}$): 3460 2 OH, 3295 and 3250 shoulders 2OH and 2NH, 1726 2CO ester, 1608 amide (1° bond), 1607 and 1615 phenyl moiety, 1545 amide (2° bond), 1158,922,830 characteristic bands.

3. $H^1$ N.M.R. spectrum (solvent: $CDCl_3 + 1\%$ D.M.S.O.; internal reference T.M.S.;δp.p.m.); 7.5÷7.25 and 6.85÷6.6 (4H; aromatic hydroeus), 5.66 c.a. (1H=CH), 5.20 c.a. (1H; $W_{\frac{1}{2}}=8Hz$; $\overline{CHOO}/$ ), 2.63 b.s. (4H; OC—$CH_2$—$CH_2$—CO), 1.65 b.s. (3H; C=C=$CH_3$), 23 1.3 c.a. (5H; C—$CH_2$—CH—CH-2—C—O), 1.12 and 1.09 s. (3H each; gem. $CH_3$).

Legend:
c.a;=complex absorption
b.s.=broadened singulet
s.=singlet
T.M.S.=Tetramethylsilane
D.M.S.=Dimethylsulphoxide
$W_{\frac{1}{2}}$=broadness at half height 4. Mass spectrum (quadrupole, direct insertion, 80 eV, 70 mA; m/z): 961 [M+; 0.3%]; 348[(M-18)+; 0.2%]; 282 (0.15%); 261 (3); 243 (2); 228 (0.8); (209 8); 200(3); 191(8); 163(2); 152 (10) 137(15); 119(5); 109 base peak; 94(40); 93(45); 91 (17); 79(77); 59(32).

ACUTE TOXICITY

Method of studying $LD_{50}$ in the mouse after a single oral administration.

Groups of 10 Swiss albine, female, adult mice (20–22g), fasting from the evening preceding the test, are treated orally with various doses (4 to 5) of the test drugs, dissolved/suspended in 1% hydroxycellulose (volume administered ; 20 ml/kg).

Thereafter, the animals are fed again (Morini MIL fodder for mice).

The 50% lethal dose ($LD_{50}$) is calculated by the method Litchfield J. T. and Wilcoxon F. (J. Pharmacol 96,99–113, 1949) by utilizing the mortality data as obtained at 14th day after the drug treatment.

TABLE No. 1

| Acute toxicity in the mouse after oral administration. | |
|---|---|
| Substance | $LD_{50}$ in mg/kg |
| CO/1499 | 2070 |
| d,l-trans-sobrerol | 2340 |

TABLE No. 1-continued

| Acute toxicity in the mouse after oral administration. | |
|---|---|
| Substance | $LD_{50}$ in mg/kg |
| p-aminophenol | 800[1] |

[1]The comparison with p-aminophenol in the present toxicity test serves only to give a measure of the difference, enormously favourable for the amide derivative of this invention.

BRONCHOSECRETAGOGUE ACTIVITY

Method of mucoproduction in the rabbit according to Scuri R. et al Boll. Chem. Farm. 119, 181–7, 1980.

Male brown rabbits weighing 2.8–3.5 kg are used. To said animals, by a surgical operation under anaesthesia, a T shaped tracheal cannula is applied, as described in the above bibliographic reference.

To the cannula, a container ( a polypropylene 2 ml test tube) is applied for periodical collection of the bronchial secretion. The study of mucoproduction, started at the fourth day after the operation, is divided into two 4 hour periods for collecting and measuring the mucus, and precisely from 8:30 to 12:30 (I), and from 12:30 to 16:30 (II).

The activity of each drug is tested by administering the same by oesophageal way (os) at the beginning of the II period and by evaluating the percent increase of mucoproduction (weight of the mucus as collected) in the II period as compared with the I period.

TABLE No. 2

| Bronchosecretagogue activity in the rabbit Oral drug administration. | |
|---|---|
| Substance | Activity |
| CO/1499* | 131 |
| d,l-trans-sobrerol | 100 |
| p-aminophenol | 0 |

*The activity of the compound of formula (I) of the present invention is based on the d,l-trans-sobrerol, taken equal to 100.

FLUIDIZING "IN VIVO" ACTIVITY

Method for studying viscosity of the bronchial mucus of a bronchitic rabbit (R. Scuri et al—Il Farmaco, Ed. Pr., 36, 36–48, 1981).

Male rabbits weighing 2.7–3.5 kg., made bronchitic by sulphuric acid aerosol treatment according to the method of Cantarelli (G. Cantarelli et al—Il Farmaco, Ed. Pr. 34,393–416, 1979) are treated with the test drug and the bronchial mucus is collected by means of a tracheal cannula according to the procedure of R. Scuri (R. Scuri et al.—Boll. Chim. Farm. 119,181–7, 1980). The viscosity of the mucus as withdrawn is studied by using a Contraves RM16 microviscosimeter and it is recorded by a Rheomat 15 T-FC apparatus.

TABLE No. 3

| Fluidizing "in vivo" activity of bronchial mucus of bronchitic rabbits. Oral drug administration. | |
|---|---|
| Substance | Activity |
| CO/1499* | 120 |
| d,l-trans-sobrerol | 100 |
| p-aminophenol | 0 |

*The activity of the compound of formula (I) of this invention is based on the d,l-trans-sobrerol, taken equal to 100.

ANTIPYRETIC ACTIVITY

Method for studying the antipyretic activity in the rat.

Albino Wistar female rats, weighing 100–140g, are utilized. The animals having a rectal, basal temperature from 36° to 37° C. are selected.

The test substances are administered by oral way contemporaneously with the pyretic agent (dry yeast, suspended in water at the 20% concentration; volume administered 15 ml/kg subcutaneously) at groups of 5 animals per dose.

After 4,5,6,7 and 25 hours from the treatment, the rectal temperature of the animals is measured by an Ellab RM6 probe, connected to an Ellab mod. TE-3 thermometer.

The activity of the drugs is evaluated by utilizing a temperature index which is provided by the algebraic sum of the differences in the rectal temperature between the measure values at the various times and the basal value.

TABLE No. 4

| Antipyretic activity in the rat after oral administration. | |
| --- | --- |
| Substance | Activity |
| CO/1499* | 127 |
| p-aminophenol | 100 |
| d,l-trans-sobrerol | 0 |

*The activity of the compound of formula (I) of this invention is based on the p-aminophenol, taken equal to 100.

Pharmacocinetics

For this study, two groups of Wistar rats (170 280 g), fasting about 15 hours before treatment, are utilized. The animals were allowed to drink an aqueous 10% glucose solution. To the rats, the compound of formula I, by oral way (transoesophageal intubation) is administered at the dose of 400 mg/kg (a single administration) and at 0.5 h; 1 h; 1.5 h; 2 h; 3 h; 4 h; 6 h from administration, 5 rats/time are sacrificed. The blood, as collected into test tubes containing sodium heparin, is centrifuged and the plasma so obtained is utilized for quantitative analysis of the compound of formula (I) of the invention by means of high pressure liquid chromatography (HPLC) with an U.V. detector. The course of the plasmatic levels has pointed out a quick and good absorption of the drug.

In relation to the activity showed by the compound of formula (I) of the present invention, this as a mucoscretolytic-fluidizing-antipyretic, the present invention further provides pharmaceutical compositions containing the compound of formula (I) of this invention in dosage units.

The pharmaceutical forms containing said active components are preferably those for oral and rectal administration, and particularly: capsules, tablets, syrup, granules in little bags and suppositories. As excipients one may employ, for the oral pharmaceutic forms: starch, lactose, microgranular cellulose, sorbitol, polyethylene glycol and more generally, diluent, bonding, lubricating, aromatizing, flavour masking and sweetening agents.

For the suppository form, as excipients, triglycerides of saturated fatty acids, lecithins or phospholipids of more common pharmaceutical use are employed.

I claim:

1. 5-[3-[N - (4-hydroxyphenyl) carboxamido]-1-oxopropoxy]-α,α- 4-trimethyl-3-cyclohexene-1-methanol, of formula:

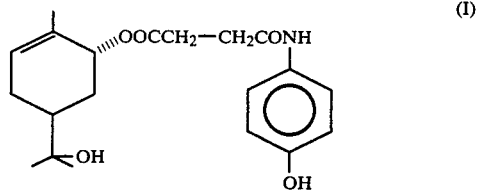

2. A pharmaceutical composition having mucosecretolytic-fluidizing and antipyretic activity characterized in that it comprises a mucosecretolytic-fluidizing and antipyretic activity effective amount of the compound of formula (I) of claim 1 and at least one pharmaceutically acceptable vehicle or excipient.

3. A method of treating a respiratory disease characterized in that it comprises administering to a host having a respiratory disease a mucosecretolytic-fluidizing and antipyretic effective amount of the compound of formula (I) of claim 1.

* * * * *